(12) United States Patent
Chen et al.

(10) Patent No.: US 11,992,199 B2
(45) Date of Patent: May 28, 2024

(54) VALVE LEAFLET OBSTRUCTION REPAIR CLIP AND REPAIR SYSTEM THEREOF

(71) Applicant: Shanghai ConFlow MedTech Co., Ltd., Shanghai (CN)

(72) Inventors: Xiumin Chen, Shanghai (CN); Qing Li, Shanghai (CN); Baicheng Hu, Shanghai (CN)

(73) Assignee: Shanghai ConFlow MedTech Co., Ltd., Shanghai (CN)

( * ) Notice: Subject to any disclaimer, the term of this patent is extended or adjusted under 35 U.S.C. 154(b) by 0 days.

(21) Appl. No.: 18/556,447

(22) PCT Filed: Nov. 14, 2022

(86) PCT No.: PCT/CN2022/131648
§ 371 (c)(1),
(2) Date: Oct. 20, 2023

(87) PCT Pub. No.: WO2024/065977
PCT Pub. Date: Apr. 4, 2024

(65) Prior Publication Data
US 2024/0108322 A1    Apr. 4, 2024

(30) Foreign Application Priority Data
Sep. 30, 2022 (CN) .......................... 202211218126.7

(51) Int. Cl.
*A61B 17/00* (2006.01)
*A61F 2/24* (2006.01)

(52) U.S. Cl.
CPC ........ *A61B 17/0057* (2013.01); *A61F 2/2463* (2013.01); *A61F 2/2466* (2013.01);
(Continued)

(58) Field of Classification Search
CPC ....... A61B 17/0057; A61B 2017/00584; A61F 2/2454; A61F 2220/0016; A61F 2/246; A61F 2/2442; A61F 2/2463; A61F 2/2466
See application file for complete search history.

(56) References Cited

U.S. PATENT DOCUMENTS 10,478,304 B2 * 11/2019 McNiven ................ A61F 2/246
10,667,815 B2 *  6/2020 Krone .............. A61B 17/00234
(Continued)

FOREIGN PATENT DOCUMENTS

CA         3136334 A1     10/2020
CN        111772874 A     10/2020
(Continued)

OTHER PUBLICATIONS

International Search Report issued in corresponding PCT Application No. PCT/CN2022/131648, dated Jun. 30, 2023.
(Continued)

*Primary Examiner* — Ariana Zimbouski
*Assistant Examiner* — Rachel S Highland
(74) *Attorney, Agent, or Firm* — Westbridge IP LLC

(57) ABSTRACT

A valve leaflet obstruction repair clip and a repair system thereof include a clamping component and a flow obstruction component. The clamping component and the flow obstruction component are assembled and clamped to fix the incomplete closure between the valve leaflets. The upper clamping arm and the lower clamping arm are engaged together in a natural state, and the upper clamping arm undergoes unilateral movement in an extended state. The present application enables edge-to-edge repair of the valve leaflets and adopts unilateral clamping, effectively preventing the problem of valve leaflet stenosis caused by the implantation of the repair device.

3 Claims, 8 Drawing Sheets

(52) U.S. Cl.
CPC ... *A61B 2017/00584* (2013.01); *A61F 2/2442* (2013.01); *A61F 2/2454* (2013.01); *A61F 2/246* (2013.01); *A61F 2220/0016* (2013.01)

(56) References Cited

U.S. PATENT DOCUMENTS

| | | | |
|---|---|---|---|
| 11,207,181 B2* | 12/2021 | Freschauf | ............... A61F 2/246 |
| 2019/0000613 A1* | 1/2019 | Delgado | ................ A61B 17/00 |
| 2019/0261995 A1* | 8/2019 | Goldfarb | ............ A61B 17/1285 |
| 2022/0133327 A1* | 5/2022 | Zhang | ............... A61B 17/1285 |
| | | | 606/142 |

FOREIGN PATENT DOCUMENTS

| | | |
|---|---|---|
| CN | 113288515 A | 8/2021 |
| CN | 113679512 A | 11/2021 |
| CN | 113796993 A | 12/2021 |
| WO | 2021228099 A1 | 11/2021 |

OTHER PUBLICATIONS

Written Opinion issued in corresponding PCT Application No. PCT/CN2022/131648, dated Jun. 30, 2023.

* cited by examiner

VALVE LEAFLET OBSTRUCTION REPAIR CLIP AND REPAIR SYSTEM THEREOF

CROSS-REFERENCE TO RELATED APPLICATIONS

This application is a national stage of International Application No. PCT/CN2022/131648, filed on Nov. 14, 2022, which claims priority to Chinese Patent Application No. 202211218126.7, filed on Sep. 30, 2022. All of the aforementioned applications are incorporated herein by reference in their entireties.

TECHNICAL FIELD

The present application relates to the field of medical devices, specifically to a valve leaflet obstruction repair clip and a repair system thereof.

BACKGROUND

In recent years, numerous interventional devices for treating mitral or tricuspid regurgitation have been developed by medical device manufacturers both domestically and internationally. The main methods for treating mitral or tricuspid regurgitation include edge-to-edge repair techniques, annuloplasty techniques, annular reshaping techniques, and chordal repair techniques. Among them, the edge-to-edge repair technique has shown good safety. The MitraClip (CN 102395331B) by Abbott and the PASCAL (US 2019/0321166A1) by Edwards are typical examples of edge-to-edge repair techniques that have been widely used in the market. These devices typically fix the implant at the distal end of the interventional catheter and deliver it to the desired implantation site through a matching delivery sheath. During this process, the operator uses modern medical imaging techniques to accurately guide the device to the location where the regurgitation needs to be blocked. Taking the mitral valve as an example, when implanting the edge-to-edge repair device, the anterior and posterior valve leaflets of the mitral valve need to be grasped together to solve the problem of mitral valve leakage and regurgitation through mechanical clamping.

However, on the other hand, the edge-to-edge repair device may cause valve leaflet stenosis after implantation. After implantation, the clip fixes the free edge of the valve leaflet, making the valve leaflet more closely approximated during late systole, reducing the possibility of regurgitation. However, during diastole, when the valve leaflet needs to open to allow blood flow from the atrium to the ventricle, the clamping of the clip may restrict the opening of the valve leaflet, resulting in valve leaflet stenosis.

SUMMARY

Given the above technical problems, the present application provides a valve leaflet obstruction repair clip and repair system thereof, comprising:
 a clamping component and a flow obstruction component, the clamping component and the obstruction component being assembled and clamped and fixed at the incomplete closure between the valve leaflets.
 The clamping component includes an upper clamping arm, a lower clamping arm, a fixing component, a supporting component, and a connecting component.

The upper clamping arm and the lower clamping arm are engaged together in their natural state, and the upper clamping arm performs unilateral movement in the extended state.

The connecting component is provided with an installation groove, and the upper clamping arm, lower clamping arm, and supporting component are fixedly overlapped in the installation groove and extend from the lower side of the installation groove.

The fixing component is located on the lower surface of the lower clamping arm and is used to fix the obstruction component.

The lower part of the supporting component is accommodated inside the obstruction component and is used to support the obstruction component.

After the clamping component and the obstruction component are assembled, they are used to hold and fill the incomplete closure between the valve leaflets, thereby preventing backflow; a clamping opening is formed between the upper clamping arm and the lower clamping arm. The operation of the clamp and repair requires the cooperation of a driving mechanism, which is used to control the opening and closing of the clamping opening. In the natural state, the upper clamping arm is engaged with the lower clamping arm. The natural state refers to the state in which the upper clamping arm and the lower clamping arm are assembled and formed after processing. In contrast, there are also the retrieval state, extended state, and closure state in the clamp and repair. In the retrieval state, natural state, and closure state, the upper clamping arm and the lower clamping arm are closed. In the extended state, the upper clamping arm and the lower clamping arm are opened, and the opening of the clamping opening is achieved by controlling the unilateral rotation of the upper clamping arm. The closure of the clamping opening in the closure state is also achieved by controlling the unilateral rotation of the upper clamping arm. This unilateral clamping design effectively overcomes the problem of valve leaflet narrowing during the diastolic phase after the implantation of the repair instrument.

Preferably, the main structure of the obstruction component is an enlarged obstruction body, and the surface of the obstruction body is covered with an obstruction membrane.

The overall appearance of the obstruction component is flask-shaped, and when the instrument is clamped, the obstruction component is close to being upright in the closed state of the upper and lower clamping arms, and the middle part of the obstruction component corresponds to the joint surface of the valve leaflets, thereby achieving better obstruction effect.

Preferably, the obstruction component is internally provided with a support ring, and the upper end of the support ring is connected to the fixing component. The support ring and the supporting component constitute the skeleton of the obstruction component, and the skeleton, together with the fixing component, stretches and expands the obstruction membrane to the expected shape.

The skeleton can provide support after the obstruction component is implanted, ensuring that it can stably fill the incomplete closure of the valve leaflets and achieve reliable obstruction function. It increases the overall toughness of the obstruction membrane and prevents deformation or displacement of the obstruction component relative to the clamping component caused by blood flow erosion. It also assists in positioning the lower clamping arm.

Preferably, the transverse section of the obstruction body is an obstruction section, and the obstruction section has the maximum thickness and width throughout the obstruction body.

The shape of the obstruction component can be varied. In addition to the flask shape, it can also be square, circular, or a combination of multiple shapes. The obstruction section can also be designed as circular, elliptical, or a combination of multiple curves. There is also a fully wrapped obstruction component. Although the shapes of these obstruction components are different, they all need to ensure that they have the maximum thickness and width to achieve the best obstruction effect after implantation.

Preferably, the clamping component is sutured with a layer of woven cover film, and the woven cover film and the obstruction membrane are made of biocompatible polymer membranes.

Untreated synthetic polymer materials can cause strong immune rejection reactions when they enter the human body. Biocompatible polymer materials have high compatibility with human tissue cells, are non-carcinogenic, and have no other adverse reactions. The repair clip acts on the mitral valve or tricuspid valve. Therefore, more specifically, the polymer membrane here is a biocompatible polymer membrane with good blood compatibility in biocompatibility evaluation, which can effectively improve the endothelialization rate of the instrument after implantation.

Preferably, the ratio of the distance between the fixing component and the distal edge of the lower clamping arm to the total length of the lower clamping arm is 0.5-0.75.

The purpose of the positioning requirement for the fixing components is to ensure the extended effect and support the stability of the obstruction material. If the fixing component is positioned too low, the obstruction material will not be able to fully open, greatly reducing the obstruction effect. If the installation position is too high, the tension of the obstruction material will be too high and the obstruction membrane will lack flexibility.

Preferably, the upper clamping arm, lower clamping arm, and support component are composed of fixed sections and free sections, and the fixed sections of the three components are sequentially overlapped and fixed in the installation groove by pressing or welding.

By fixing the fixed sections of the three components in a sequential overlapping manner, the overall volume of the repair clip can be reduced, and the free sections of the upper clamping arm and lower clamping arm can be kept on the same symmetrical plane, facilitating the alignment of the clamping surfaces of the two components and achieving stable clamping.

Both pressing and welding are methods of fixed connection, and both methods can effectively reduce the use of excessive fixing components.

Preferably, in the natural state, the angle between the fixed section of the upper clamping arm and its free section is acute, and in the extended state, the free section is pulled towards the fixed section.

The extended state is a preparatory state for the repair clip, where the free section of the upper clamping arm changes from being in contact with the surface of the lower clamping arm to being in contact with the fixed section. The lower clamping arm remains stationary throughout the process, relying only on the one-sided movement of the upper clamping arm to achieve extension. Additionally, in this application, the angle refers to the inner angle.

Preferably, a pressure plate is cut out at the bottom of the free section of the upper clamping arm, and the pressure plate is bent inward to form the fixed section of the upper clamping arm, leaving a cavity in the original position of the free section.

The fixed section of the upper clamping arm is formed by cutting and bending a portion of the free section, reducing processing materials and fully utilizing the plasticity of the material. In this processing method, the direction of the tension exerted on the upper clamping arm during the counterclockwise movement from the free section to the fixed section is the same as the direction of its elastic deformation. This prevents stress fatigue at the bending point due to frequent adjustments during surgery, increases the cyclic bending period of the upper clamping arm, and improves the anti-fatigue effect of the structure.

Preferably, the fixed section of the lower clamping arm is V-shaped with the free section, and the fixed section of the lower clamping arm passes through the cavity on the free section of the upper clamping arm and is fixed in the installation groove.

The V-shaped structure of the lower clamping arm is fixed through the free section of the upper clamping arm, resulting in a crossed or X-shaped fixed state between the upper and lower clamping arms. Compared to the parallel fixed method of the upper and lower clamping arms, the X-shaped fixed method allows for a tighter fit between the clamping surfaces of the upper and lower clamping arms, thereby increasing the clamping force on the target tissue and the stability of capturing valve leaflets during surgery.

Preferably, the upper clamping arm is equipped with serration facing the lower clamping arm.

The serration enhances the stability of clamping the valve leaflets by the upper and lower clamping arms, which is the same goal pursued by the V-shaped structure of the lower clamping arm mentioned above.

Preferably, the upper clamping arm, lower clamping arm, and support are cut and processed into shape using shape memory nickel-titanium alloy sheets.

Shape memory nickel-titanium alloy sheets have good plasticity and also possess advantages such as wear resistance, corrosion resistance, high damping, and super elasticity. Their corrosion resistance is superior to the best medical stainless steel currently available, which effectively meets the requirements of the single-sided clamping action of the upper clamping arm in the present application.

Preferably, the material of the woven covering film and the obstruction film is PET or PTFE.

In addition to polytetrafluoroethylene (PTFE) and polyethylene terephthalate (PET), also known as polyester resin, other materials such as polylactic acid (PLA) can be used. The above-mentioned materials exhibit inertness after implantation in the body, causing no severe physiological reactions and being difficult to degrade. They are non-toxic and harmless.

The present application also provides a valve leaflet obstruction repair clip repair system, which includes the aforementioned valve leaflet obstruction repair clip or conventional valve leaflet clip and its driving mechanism. The conventional valve leaflet clip is a conventional device in the prior art that clips onto the valve leaflet using clamping force. The valve leaflet obstruction repair clip or conventional valve leaflet clip is the implanted part of the system, and the driving mechanism inserts the implanted part into the target position.

The driving mechanism includes a dissociation device, a dissociation rod, and a pull wire.

The dissociation device includes a second connecting piece, a receiving groove for accommodating the implanted part, and a dissociation groove. The tail end of the second connecting piece is connected to the conduit of the delivery system. The second connecting piece has a dissociation rod hole, through which the dissociation rod is inserted from the conduit and then fixed to the far end of the implanted part and the pull wire.

The distal end of the pull wire is located on the dissociation device, and the other end passes through and connects to the control point of the clamping component before connecting to the control point of the dissociation rod. By controlling the pulling and releasing at the control point, the clamping component can be opened and closed.

The dissociation groove is located below the receiving groove, and the side walls of the dissociation groove have holes. The dissociation rod is inserted into the holes to position it in the dissociation groove. The distal end of the pull wire is wound around the dissociation rod in the dissociation groove.

The driving mechanism delivers the repair clip into the target position of the mitral or tricuspid valve through minimally invasive means via the femoral vein. The dissociation device controls the opening and closing of the clamping arms, and the closure and release are adjusted by manipulating the pull wire. The repair clip is delivered into the body through an external sheath, and the receiving groove effectively reduces the volume of the repair clip. During delivery, the repair clip is contained within the receiving groove, reducing the delivery size and facilitating compatibility with smaller delivery sheaths.

Preferably, there is a groove below the dissociation groove, and the side end of the first connecting piece of the valve leaflet obstruction repair clip has a protrusion with a through-hole. The groove is matched with the protrusion, and the protrusion is accommodated in the groove. The dissociation rod passes through the through-hole and the groove to fix the protrusion in the groove.

The purpose of the dissociation rod passing through the through-hole of the protrusion is to fix the implanted part on the dissociation device. After the implantation of the implanted part is completed, the dissociation rod is pulled upward to pull it out of the through-hole of the protrusion, thereby separating the dissociation device from the implanted part. This design allows for convenient separation of the implanted part.

Preferably, the control point of the implanted part is located on the upper clamping arm, and there is a pull ring on the upper clamping arm. The pull ring mentioned here can be a position where a pull wire passes through the upper clamping arm. The distal end of the pull wire forms a loop, and the loop passes through the pull ring and is connected to the dissociation rod in the dissociation groove.

During the adjustment of the clamping process, the rotation of the free section of the upper clamping arm is controlled by the loop of the pull wire. After the implantation is completed, the dissociation rod is retracted to detach the dissociation device from the clamping component. The dissociation rod is further retracted, and the distal end of the pull wire is released from the dissociation rod. After retracting the pull wire from the control point above, the entire implanted part is released.

In this application, the pull wire is not directly threaded through the upper clamping arm. Instead, a pull ring is used as an intermediary. Compared to direct contact with the upper clamping arm, this structure allows for smoother retraction of the pull wire. Additionally, the pull wire does not directly touch the clamped valve leaflet, preventing any interference with the clamping effect of the valve leaflet due to the retraction of the pull wire.

Advantages:
1. This application enables edge-to-edge repair of the valve leaflet, while using unilateral clamping to effectively prevent valve leaflet stenosis caused by the implantation of repair devices.
2. The flow obstruction structure in this application reliably reduces problems such as insufficient valve leaflet closure and regurgitation in patients.

BRIEF DESCRIPTION OF THE DRAWINGS

The following is a further explanation of the present application concerning the accompanying drawings.

DETAILED DESCRIPTION OF THE EMBODIMENTS

Figure 1:
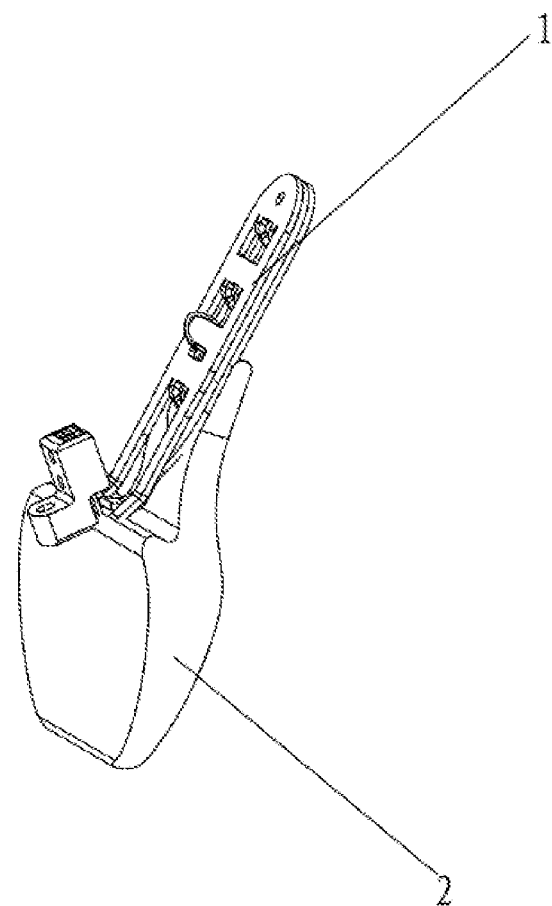
FIG. 1 shows a schematic diagram of the valve leaflet obstruction repair clip in this application.
Figure 2:
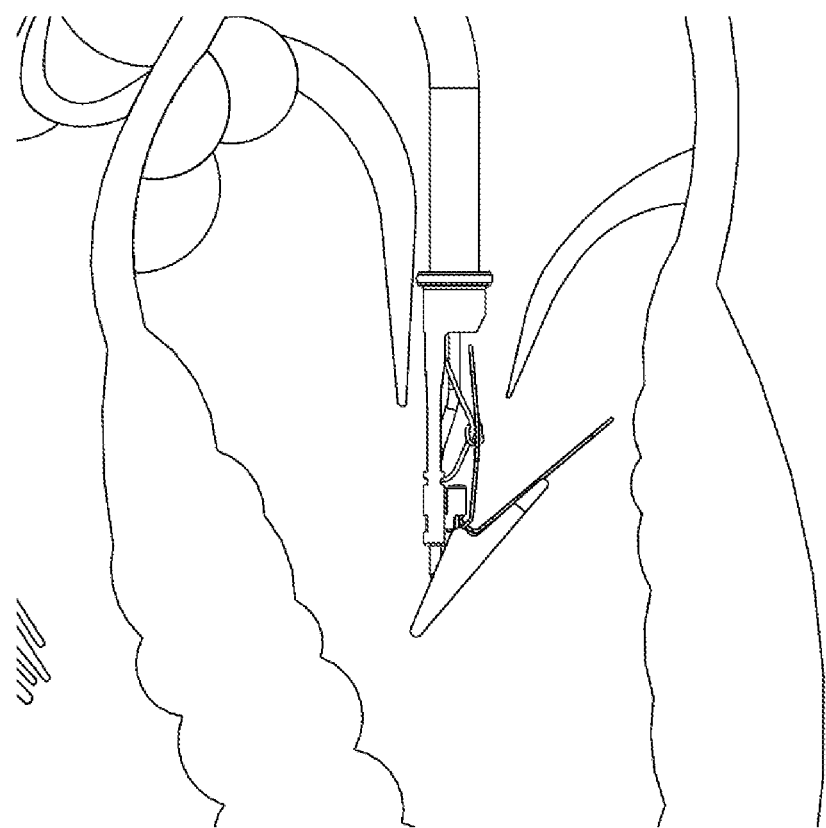
FIGS. 2-3 illustrate the clamping process of the valve leaflet obstruction repair clip in this application.
Figure 3:
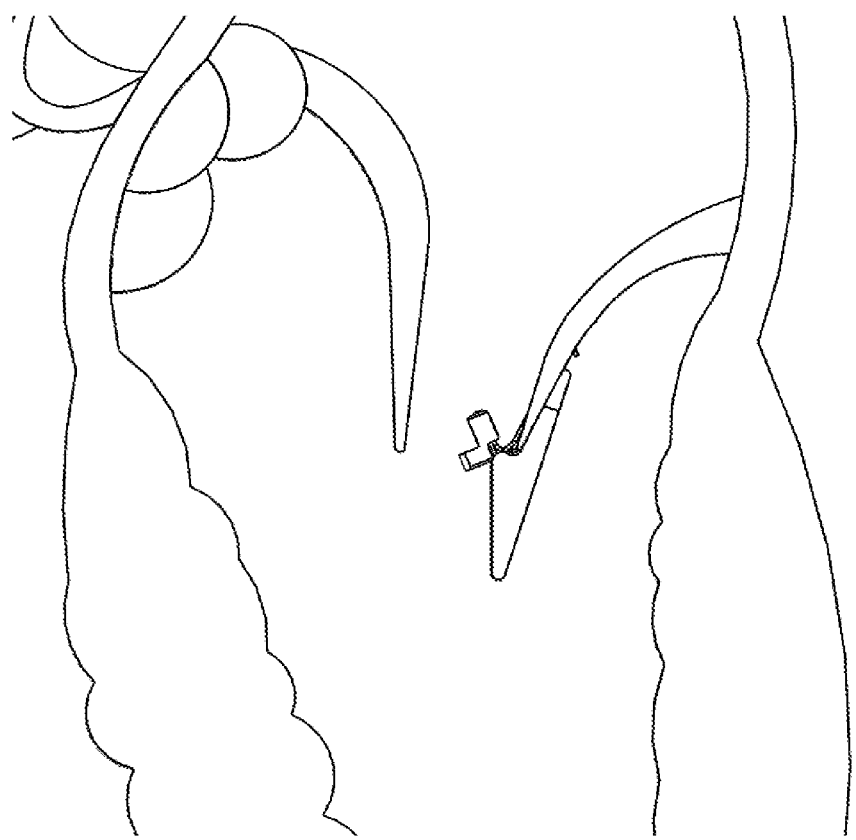
Figure 4:
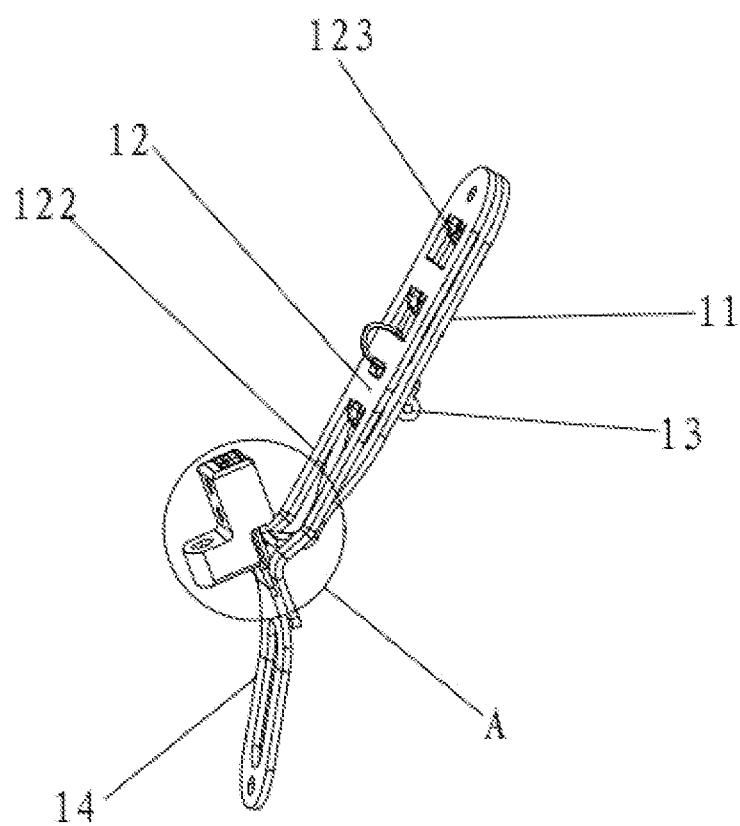
FIG. 4 shows a schematic diagram of the clamping component in this application.
Figure 5:
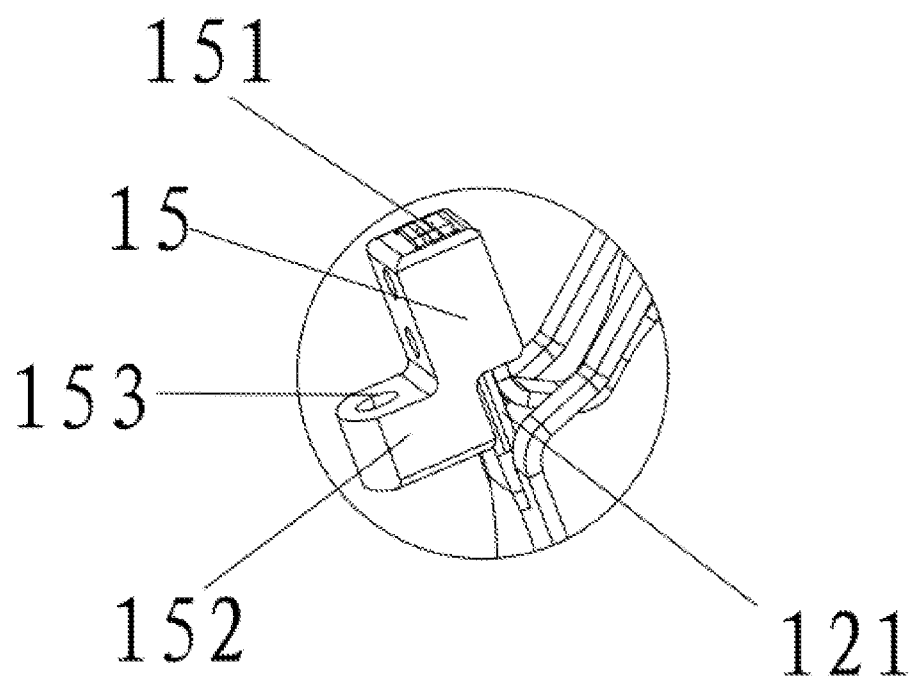
FIG. 5 is an enlarged view of section A in FIG. 4.
Figure 6:
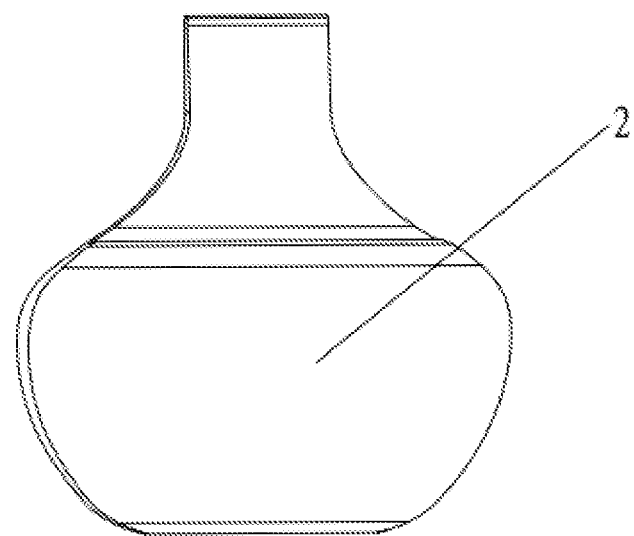
FIG. 6 shows a schematic diagram of the flow obstruction component in this application.

The following will describe the technical solution of the embodiments of the present application clearly and completely, concerning the accompanying drawings. It should be understood that the described embodiments are only part of the embodiments of the present application, and not all embodiments. Based on the embodiments of the present application, all other embodiments obtained by those skilled in the art without creative labor are within the scope of protection of the present application.

In the description of the present application, it should be understood that the terms "front," "rear," "left," "right," "up," "down," and the like indicate the orientation or positional relationship based on the orientation or positional relationship shown in the accompanying drawings. It is for the convenience of describing the present application and simplifying the description and does not indicate or imply that the device or element referred to must have a specific orientation, construct, and operate in a specific orientation. Therefore, it should not be understood as limiting the present application.

As shown in FIGS. 1-6, the present application provides a valve leaflet obstruction repair clip and its repair system, including a clamping component 1 and a flow obstruction component 2. The clamping component 1 is integrally assembled with the flow obstruction component 2 and clamps and fixes the closure insufficiency of the valve leaflets. The clamping component 1 includes an upper clamping arm 12, a lower clamping arm 11, a fixing piece 13, a support piece 14, and a first connecting piece 15. The upper clamping arm 12 and the lower clamping arm 11 are clamped together in a natural state and undergo unilateral movement in an extended state.

The first connecting piece 15 is provided with a mounting groove 151, and the upper clamping arm 12, the lower clamping arm 11, and the support piece 14 are overlapped and fixed to the proximal end of the first connecting piece 15 and extend from the bottom of the mounting groove 151. The fixing piece 13 is located on the lower surface of the lower clamping arm 11 and is used to fix the flow obstruction component 2. The lower part of the support piece 14 is accommodated inside the flow obstruction component 2 and is used to support the flow obstruction component 2.

After the clamping component 1 and the flow obstruction component 2 are assembled, they are clamped and fixed to fill the closure insufficiency of the valve leaflets, thereby preventing regurgitation. There is a clamping opening formed between the upper clamping arm 12 and the lower clamping arm 11. The repair clip needs to be operated in conjunction with a driving mechanism, which controls the opening and closing of the clamping opening. In the natural state, the upper clamping arm 12 is clamped together with the lower clamping arm 11. The natural state refers to the state in which the upper clamping arm 12 and the lower clamping arm 11 are assembled and formed after processing. In contrast, the repair clip also has a retracted state, an extended state, and a closed state. In the retracted state, natural state, and closed state, the upper clamping arm 12 and the lower clamping arm 11 are closed. In the extended state, the upper clamping arm 12 and the lower clamping arm 11 are open, and the opening of the clamping opening is achieved by controlling the unilateral rotation of the upper clamping arm 12. The closure of the clamping opening in the closed state is also achieved by controlling the unilateral rotation of the upper clamping arm 12. This unilateral clamping design effectively overcomes the problem of valve leaflet stenosis during diastole caused by the implantation of repair devices.

The main structure of the flow obstruction component 2 is a bulging flow obstruction body, and the surface of the flow obstruction body is covered with a flow obstruction membrane.

The overall appearance of the flow obstruction component 2 is flat and pot-shaped. When the device is clamped, in the closed state of the upper and lower clamping arms, the flow obstruction component 2 is brought close to an upright position and the middle part of the flow obstruction component 2 corresponds to the sealing surface of the valve leaflets, thereby achieving better flow obstruction effect.

The flow obstruction component 2 is internally equipped with a support ring (not shown in the figure), and the upper end of the support ring is connected to the fixing piece 13. The support ring and the support piece 14 form the skeleton of the flow obstruction component 2. The skeleton, together with the fixing piece 13, stretches and expands the flow obstruction membrane to the expected shape.

The skeleton provides support after the implantation of the flow obstruction component 2, ensuring that it can stably fill the closure insufficiency of the valve leaflets and achieve reliable flow obstruction function. It increases the overall toughness of the flow obstruction membrane and prevents deformation or displacement of the relative clamping component 1 due to the impact of blood flow. It also assists in positioning the lower clamping arm 11.

The transverse section of the flow obstruction body is the flow obstruction section, which has the maximum thickness and width throughout the flow obstruction body.

The shape of the flow obstruction component 2 can be varied. In addition to the flat pot shape, it can also be square, circular, or a combination of various shapes. The flow obstruction section can also be designed as circular, elliptical, or a combination of various curves. Additionally, there is a fully enveloping form of the flow obstruction component 2. Although these flow obstruction components 2 have different shapes, they all need to ensure the maximum thickness and width to achieve the best flow obstruction effect after implantation.

The clamping component 1 is externally sutured with a layer of woven overlay, and the woven overlay and the flow obstruction membrane are made of biocompatible polymer materials.

Unmodified synthetic polymers can elicit strong immune rejection reactions when introduced into the human body. However, biocompatible polymers have a high compatibility with the tissues and cells of the human body, and they are non-carcinogenic and do not cause adverse reactions. The clamping component acts on the mitral or tricuspid valve. Therefore, specifically, the polymer membrane used here should be a biocompatible polymer membrane with good blood compatibility, which can effectively enhance the endothelialization rate of the device after implantation.

The length ratio between the fixing piece 13 and the distal edge of the lower clamping arm 11 is 0.5-0.75 of the total length of the lower clamping arm 11.

The positioning of the fixing piece 13 is intended to ensure the extended effect and support stability of the flow obstruction body. If the fixing piece 13 is positioned too low, the flow obstruction body cannot be fully stretched and opened, greatly reducing the flow obstruction effect. If the fixing piece 13 is positioned too high, the tension on the flow obstruction body will be too high, and the flow obstruction membrane will lack toughness.

The upper clamping arm 12, lower clamping arm 11, and support piece 14 are all composed of a fixed section 121 and a free section 122, and the fixed sections of the three components are sequentially overlapped and fixed in the mounting groove 151 by pressing or welding.

By sequentially overlapping the fixed sections 121, the overall volume of the clamping component can be reduced, and the free sections of the upper clamping arm 12 and lower clamping arm 11 can be kept in the same symmetrical plane, facilitating alignment of the clamping surfaces and achieving secure clamping.

Both pressing and welding are effective methods of fixation, and both can reduce the use of excessive fixing components.

The upper clamping arm 12 consists of a fixed section 121 and a free section 122. In its natural state, the angle between the fixed section 121 and the free section 122 is acute. In the extended state, the free section 122 is pulled towards the fixed section 121 and comes into close contact with it.

The extended state is a preparatory state for the clamping of the repair. The free section 122 of the upper clamping arm 12 changes from being in contact with the upper surface of the lower clamping arm 11 to being in contact with the fixed section 121. The lower clamping arm 11 remains stationary throughout the process, relying only on the unilateral movement of the upper clamping arm 12 to achieve extension. Additionally, in this application, the term "angle" refers to the internal angle.

The fixed section and the free section of the lower clamping arm 11 form a V-shaped structure, with the fixed section of the lower clamping arm passing through the hollow of the free section of the upper clamping arm and being fixed in the mounting groove 151.

The V-shaped structure of the lower clamping arm 11, with its fixed section passing through the free section 122 of the upper clamping arm, creates a cross or X-shaped fixation between the upper and lower clamping arms. Compared to parallel fixation of the upper and lower clamping arms, the X-shaped fixation allows for a tighter fit between the clamping surfaces, increasing the clamping force on the target tissue and the stability of capturing the valve leaflets during surgery.

The upper clamping arm 12, lower clamping arm 11, and support piece 14 are cut and shaped from shape memory nickel-titanium alloy.

The shape memory nickel-titanium alloy has good malleability, as well as wear resistance, corrosion resistance, high damping, and superelasticity. Its corrosion resistance is superior to the best medical stainless steel currently available. The fixed section 121 in this application relies on the material characteristics of the nickel-titanium alloy to achieve rotational movement of the free section 122 of the upper clamping arm 12 without the need for a movable rotating component. This effectively meets the requirement of unilateral clamping of the upper clamping arm 12.

A pressure plate is cut at the bottom of the free section 122 of the upper clamping arm 12, and the pressure plate is bent inward to form the fixed section 121 of the upper clamping arm 12. The hollow is formed in the original position of the free section.

The fixed section of the upper clamping arm 12 is formed by cutting and bending a portion of the free section 122, reducing the consumption of processing materials and making full use of the malleability of the nickel-titanium alloy. In this processing method, when the free section of the upper clamping arm 12 moves counterclockwise towards the fixed section, the direction of the tension it experiences is the same as its elastic deformation direction. This prevents stress fatigue at the bending point due to frequent adjustments during surgery and improves the fatigue resistance with a larger cycle of frequent bending.

The upper clamping arm 12 is equipped with serrations 123 facing the lower clamping arm 11.

The serrations 123 enhance the stability of the clamping of the valve leaflets by the upper and lower clamping arms, serving the same purpose as the V-shaped structure of the lower clamping arm mentioned earlier.

The material of the woven covering film and the flow obstruction membrane is PET or PTFE.

In addition to polytetrafluoroethylene (PTFE) and polyethylene terephthalate (PET), the materials mentioned above, there are exceptions where other materials such as polylactic acid (PLA) can be used. These materials are inert when implanted in the body, causing no severe physiological reactions, and are not easily degraded. They are non-toxic and harmless.

Figure 7:
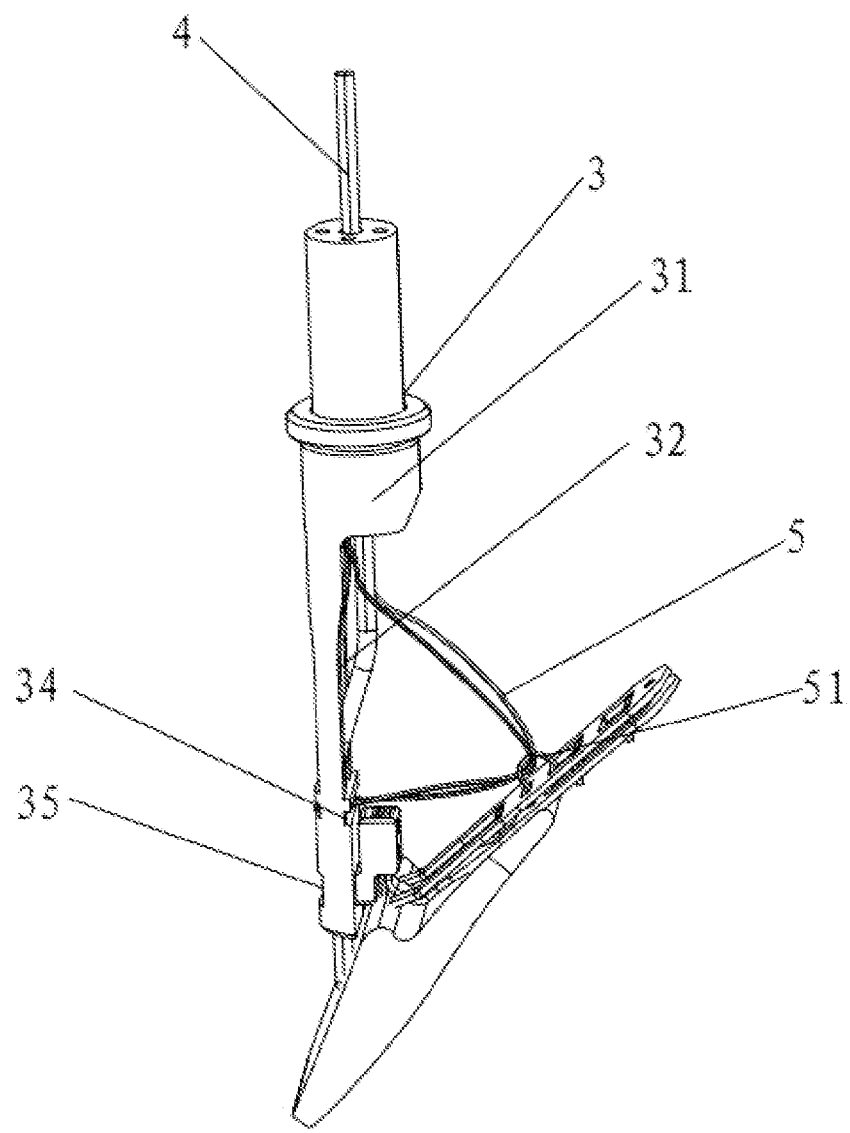
FIG. 7 shows a schematic diagram of the valve leaflet obstruction repair clip repair system in this application.
Figure 8:
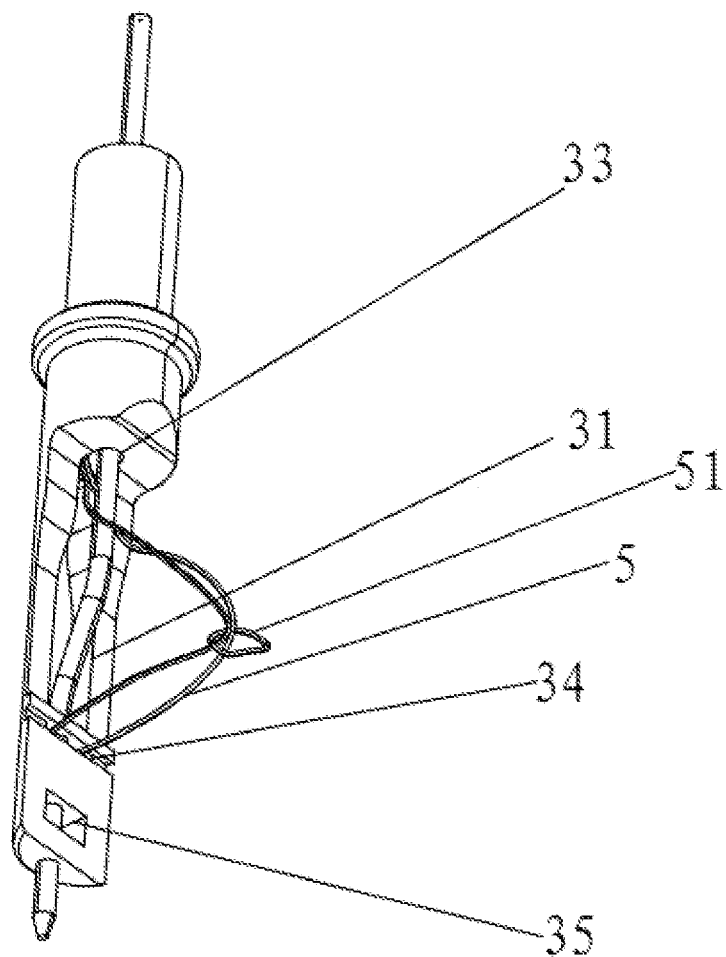
FIG. 8 shows a schematic diagram of the driving mechanism in this application.

As shown in FIGS. 7-8, the present application also provides a valve leaflet obstruction repair clip repair system, which includes the aforementioned valve leaflet obstruction repair clip or conventional valve leaflet clip and its driving mechanism. The conventional valve leaflet clip is a conventional instrument in the prior art that clamps onto the valve leaflet with clamping force. The valve leaflet obstruction repair clip or conventional valve leaflet clip is the implanted part of the system, and the driving mechanism inserts the implanted part into the target position.

The driving mechanism includes a dissociation device 3, a dissociation rod 4, and a pull wire 5. The dissociation device 3 includes a second connecting piece 31, a receiving groove 32 for receiving the implanted part, and a dissociation groove 34. The tail end of the second connecting piece 31 is connected to the lumen of the delivery system. The second connecting piece 31 has a dissociation rod hole 33, through which the dissociation rod 4 passes from the lumen and is fixed to the implanted part and the distal end of the pull wire 5. The distal end of the pull wire 5 is connected to the dissociation rod 4 in the dissociation groove 34. The other end of the pull wire 5 passes through and connects to the control point of the implanted part, and is guided to the force control point of the pull wire 5. The opening and closing of the implanted part is achieved by pulling and releasing the pull wire 5 at the control point. The dissociation groove 34 has holes on its two side walls, through which the dissociation rod 4 enters and locates in the dissociation groove 34. The distal end of the pull wire 5 is wound around the dissociation rod 4 in the dissociation groove 34.

The driving mechanism delivers the repair clip to the target position of the mitral or tricuspid valve through minimally invasive means via the femoral vein. The dissociation device 3 controls the opening and closing of the upper clamping arm 12, and the closure and release are adjusted by the pull wire 5. The repair clip is delivered into the body through an external sheath, and the receiving groove 32 effectively reduces the volume of the repair clip. During delivery, the repair clip is stored in the receiving groove 32, reducing the delivery size and facilitating compatibility with smaller delivery sheaths.

Below the dissociation groove 34, there is a recess 35, and the side end of the connecting piece 13 of the valve leaflet obstruction repair clip has a protrusion 152. The protrusion 152 has a through-hole 153, and the recess 35 is compatible with the protrusion 152. The protrusion 152 is accommodated in the recess 35, and the dissociation rod 4 passes through the through-hole 153 and the recess 35, fixing the protrusion 152 in the recess 35.

The purpose of the dissociation rod 4 passing through the through-hole 153 of the protrusion 152 is to fix the implanted part to the dissociation device 3. After the implantation operation of the implanted part is completed, pulling the dissociation rod 4 upward out of the through-hole of the protrusion 152 can separate the dissociation device 3 from the implanted part, making the operation convenient and facilitating the separation of the implanted part.

The control point of the implanted part is located on the upper clamping arm 12, and a pull ring 51 is provided on the upper clamping arm 12. The distal end of the pull wire 5 forms a loop, and the loop passes through the pull ring 51 and is connected to the dissociation rod 4 inside the dissociation groove 34.

During the adjustment of the clamping process, the rotation of the free section 122 of the upper clamping arm 12 is controlled by the loop of the pull wire 5. After the implantation is completed, the dissociation rod 4 is retracted, separating the dissociation device 3 from the engagement component 1. The dissociation rod 4 continues to retract, and the distal end of the pull wire 5 is released from the dissociation rod 4. After retracting the pull wire 5 from the control point above, the entire implanted part is released.

In this application, the pull wire 5 is not directly threaded through the upper clamping arm 12, but a pull ring 51 is used as an intermediary. Compared to directly contacting the upper clamping arm 12, this structure makes the retraction of the pull wire 5 smoother and avoids direct contact with the clamped valve leaflets, ensuring the effectiveness of valve leaflet clamping during the retraction of the pull wire 5.

The operational steps of the present application's repair system are as follows:

1. During preparation, retracting the upper clamp arm 12 into the receiving groove 32 of the dissociation device 3, folding the lower clamp arm 11 towards the distal end (i.e., the end away from the handle of the transport system) so that it can fit inside the delivery sheath. Connecting and securing the implant portion of the instrument to the dissociation device 3 using the dissociation rod 4, and retracting the implant portion of the instrument into the delivery sheath.

2. Using the transport system to deliver the repair system to the corresponding atrium (left atrium for mitral valve repair, right atrium for tricuspid valve repair).

3. Pushing the implant portion of the instrument out of the delivery sheath, controlling the retraction state of the upper clamp arm 12 using the pull wire 5, and adjusting the posture of the dissociation device 3 or repair clip by using the adjustable bending sheath to ensure that its longitudinal axis is aligned with the valve leaflet coaptation position. Rotating the clamp to ensure that the direction of the arm opening is aligned with the target valve leaflet.

4. Further delivering the repair clip into the ventricle (left ventricle for mitral valve repair, right ventricle for tricuspid valve repair).

5. Adjusting the position of the repair clip so that the target valve leaflet is resting on the lower clamp arm 11.

6. Releasing the upper clamp arm 12 to capture the valve leaflet.

7. Retracting the dissociation rod 4, releasing the implant portion, and having the upper and lower clamp arms holding the valve leaflet while the flow obstruction component 2 is blocking the position of incomplete valve leaflet closure.

8. Confirming the effectiveness of the regurgitation blockage through ultrasound and other imaging methods. If the desired goal is not achieved, retracting the upper clamp arm 12 again, adjusting the position, and recapturing the valve leaflet. If the blockage is satisfactory, releasing and retracting the corresponding pull wire 5, and implanting the repair clip.

Various modifications to these embodiments will be apparent to those skilled in the art, and the general principles defined herein may be applied to other embodiments without departing from the spirit or scope of the present invention.

What is claimed is:

1. A valve leaflet obstruction repair clip repair system, comprising a valve leaflet obstruction repair clip and a driving mechanism thereof, wherein the valve leaflet obstruction repair clip is an implantation part of the system, and the driving mechanism inserts the implantation part into a target position; and then releases the implantation part; wherein the valve leaflet obstruction repair clip comprises a clamping component and a flow obstruction component, the clamping component is integrally assembled with the flow obstruction component;

the clamping component comprises an upper clamping arm, a lower clamping arm, a fixing piece, a support piece, and a first connecting piece;

the upper clamping arm and the lower clamping arm are clamped together in a natural state, and the upper clamping arm undergoes a unilateral movement in an extended state;

the first connecting piece is provided with an installation groove, and the upper clamping arm, the lower clamping arm, and the support piece are overlapped and fixed in the installation groove from a lower side of the installation groove;

the fixing piece is located on a lower surface of the lower clamping arm and is used to fix the flow obstruction component;

a lower part of the support piece is accommodated inside the flow obstruction component and is used to support the flow obstruction component; and the driving mechanism comprises a dissociation device, a dissociation rod, and a pull wire;

the dissociation device comprises a second connecting piece, a receiving groove for accommodating the implantation part, and a dissociation groove; a tail end of the second connecting piece is connected to a lumen of a delivery system;

the second connecting piece is provided with a dissociation rod hole, and the dissociation rod passes from the lumen through the dissociation rod hole and is fixedly coupled to a far end of the implantation part and the pull wire;

a far end of the pull wire is connected to the dissociation rod in the dissociation groove; and an other end of the pull wire passes through and connects to a control point of the implantation part, leading to a pull force control area, where the implantation part is opened or closed by pulling or releasing the pull wire;

the dissociation groove having side walls provided with holes, and the dissociation rod passes through the holes to achieve positioning in the dissociation groove, with the far end of the pull wire wound around the dissociation rod in the dissociation groove.

2. The valve leaflet obstruction repair clip repair system according to claim 1, wherein a lower part of the dissociation groove is provided with a recess, and the first connecting piece of the valve leaflet obstruction repair clip is provided with a protrusion on a side end, the protrusion has a through hole, and the recess matches the protrusion, and the protrusion is accommodated in the recess, and the dissociation rod passes through the through hole and the recess to fix the protrusion in the groove.

3. The valve leaflet obstruction repair clip repair system according to claim 1, wherein the control point of the implantation part is located on the upper clamping arm, and a pull ring is provided on the upper clamping arm, and a far end of the pull wire forms a loop, which passes through the pull ring and is connected to the dissociation rod inside the dissociation groove.

* * * * *